United States Patent [19]

Solomon et al.

[11] Patent Number: 4,948,836

[45] Date of Patent: Aug. 14, 1990

[54] IMMOBILIZED ANTIBODIES

[75] Inventors: Beka Solomon, Herzellya Pituach; Eran Hadas, Rishon Lezion; Gideon Fleminger, Rehovot, all of Israel

[73] Assignee: Roehm GmbH Chemische Fabrik, Darmstadt, Fed. Rep. of Germany

[21] Appl. No.: 270,280

[22] Filed: Nov. 14, 1988

[30] Foreign Application Priority Data

Nov. 14, 1987 [DE] Fed. Rep. of Germany ....... 3738721

[51] Int. Cl.$^5$ .................. C08H 1/00; C08L 89/00; A61K 35/14
[52] U.S. Cl. .................. 525/54.1; 530/815; 530/816; 436/531; 436/532
[58] Field of Search ............ 525/54.1; 530/810, 812, 530/813, 814, 815, 816, 389; 435/177, 178, 179, 180, 181; 436/528, 529, 530, 531, 532

[56] References Cited

U.S. PATENT DOCUMENTS

| | | | |
|---|---|---|---|
| 4,210,723 | 7/1980 | Dorman et al. | 525/54.1 |
| 4,511,694 | 4/1985 | Krämer et al. | 525/54.1 |
| 4,671,958 | 6/1987 | Rodwell et al. | 530/828 |
| 4,874,813 | 10/1989 | O'Shannessy | 525/54.1 |
| 4,889,916 | 12/1989 | Packard et al. | 525/54.1 |

OTHER PUBLICATIONS

O'Shannessy et al., "Specific Conjugation Reactions of the Oligosaccharide Moieties of Immunoglobulin" Journal of Applied Biochemistry 7, 347–355 (1985).

*Primary Examiner*—Nathan M. Nutter
*Attorney, Agent, or Firm*—Oblon, Spivak, McClelland, Maier & Neustadt

[57] ABSTRACT

Antibodies which are immobilized and covalently bound to a matrix polymer by means of a modification in a carbohydrate region of the antibodies; wherein the binding of the antibodies is effected by condensing at least one aldehyde group in an oxidized carbohydrate region and at least one epoxide function of an epoxy-group-containing matrix polymer, said condensation being conducted in the presence of a bifunctional reagent which has, on one end position of a spacer unit having at least three members, an amino group capable of condensing with the aldehyde group, and which has on the other end position a group which reacts covalently with the epoxide function.

16 Claims, No Drawings

IMMOBILIZED ANTIBODIES

BACKGROUND OF THE INVENTION

1. Field of the Invention:

The present invention relates to regiospecific conjugate formation of oligosaccharide-containing antibodies by means of oxidative modification of the carbohydrate region of the antibodies.

2. Description of the Background:

The fixation of biologically active substances to substrates, for example, carrier materials etc., is one of the standard processes in biochemical research and engineering. Various techniques for this have been developed, which depend on the chemical nature of the substances to be fixed and the purpose of the fixation. See, e.g., Buchholz, K., "Characterization of Immobilized Biocatalysts", in Dechema Monographs, V. 84 No. 1724–1731, pub. Verlag Chemie (1979).

From the beginning, polysaccharides such as cellulose, starch, and dextran have been important in practice as carrier materials. Ordinarily these materials must be chemically modified for activation. A large number of modification methods have been proposed, notably the activation of starch by oxidation with periodate, wherein formyl groups are formed with cleavage of the hemiacetal ring. See Goldstein, L., Pecht, M., Blumberg, S., Atlas, D., and Levin, Y., Biochem., 9, 2322 (1979).

Coupling over the carbohydrate portion of cell membranes has been achieved, e.g., with red blood corpuscles by oxidation with periodate. The resulting reactive aldehyde groups couple with the side chain amino groups of proteins. See Sanderson, C.I., and Wilson, D.V., 1971, Immunochemistry, 8:163. Periodate oxidation of antibodies has also been used for conjugation of antibodies with enzyme markers. See Gaivoronskaya, A.G. et al., CA 95, 130787j. Similarly, in Eur. OS 0 175 617 conjugates were proposed which are formed from antibodies and therapeutic agents, which conjugates are directed against a target antigen.

U.S. Pat. No. 4,671,958 contains a method of covalent binding of "linker" groups to specific sites of antibody molecules which can be used against desired target antigens.

Eur. OS 0 088 695 describes a number of methods for covalent binding of soluble or insoluble conjugate partners, such as chemical substances, carriers, etc., to antibodies. The conjugates formed are interesting with regard to the affinity-separation and purification methods, as well as possible diagnostic and therapeutic applications. The binding may occur in particular, among others, via the carbohydrate part of the antibodies. E.g., for monoclonal immunoassays, IgM is oxidized with galactose oxidase and catalase and is then condensed with phenylhydrazine-glycyl-glycyl-arginyl-7-amino-4-methylcoumarin. See also Rodwell, J.D. et al., Proc. Nat. Acad. Sci. USA/Immunology, 83, 2632–36 (1986).

M.M Chua et al. Biochem. Biophys. Acta, 800, 3:291 (1984) also achieved binding of immunoglobulin to liposomal membranes by mild oxidation of carbohydrate groups by periodate or galactose oxidase in the constant region of the heavy chain of the immunoglobulin, to produce aldehyde functions which could then react with hydrazide groups fixed to the membrane surfaces of the liposomes.

D.J. O'Shannessy et al. also proposed specific conjugation of polyclonal and monoclonal antibodies via their carbohydrate regions. First, aldehyde groups are formed by mild oxidation, and these are converted with hydrazine derivatives of biotin, suitable fluorescing dyes or enzymes to produce stabile antibody conjugates having full immunological activity. Also, the possibility of fixing to hydrazine-modified solid substrates has also been proposed. The support used for the immune affinity chromatography is, e.g., (commercial) agarose-adipic acid hydrazide. See J. Appl. Biochem., 7, 347–355 (1985). In another publication, O'Shannessy and W.L. Hoffmann reported the use of weak acid catalyzed condensations of oxidatively formed aldehyde groups on the oligosaccharide side chains of glycoproteins with hydrazine-functionalized agarose. The latter had been produced by reacting commercial activated ester-group-containing agarose with hydrazine hydrate. See Biological Chem. Hoppe-Seyler, 368, 7:767–8 (1987).

Polymer-bound antibodies and antigens have received progressively wider use in detecting the presence of specific substances. See "Encyclopedia of Polymer Science and Technology", pub. J. Wiley, Vol. 2, pp. 55–59 (1985). Particularly noteworthy uses are the detection of special hormones, blood components, normal and abnormal cell types, and pathogens, and the detection of molecules whose presence indicates a malignant tumor. Further, monoclonal antibodies are also employed in therapy. For example, it is possible to bind lethal agents, such as toxic substances or radioisotopes, to cancer-specific antibodies, with the aim of having such complexes seek out and combine with the target cells, thereby eventually destroying the cells without permanently injuring the surrounding tissues.

However, antibodies have only limited stability with regard to pH and the ionic strength of the medium which surrounds them. Thus, chemical modification of antibodies to produce covalent fixing, e.g. to carrier materials, is almost invariably accompanied by problems. At a minimum it is necessary that such fixing cause no degradation of the combining affinity of the antibody to the antigen. For example, conventional methods of immobilizing antibodies on solid carriers by means of cyanogen bromide, N,N'-carbonyldiimidazole, periodate oxidation, or epoxide chemistry, often lead to binding via nucleophilic active groups such as, e.g., amino, thio, or hydroxy groups, near the antigen combining site, which can result in a significantly decreased combining capability. See Yim, K., Biol. Chem. Hoppe-Seyler, 386, 7:785 (1987). It has been suggested that the composition of the polymeric carrier is the decisive factor in determining its properties and suitability as a carrier. Buchholz, K., Ed., in "Characterization of immobilized biocatalysts", loc. cit., 64. Accordingly, an abundant selection of potential carrier materials exists in the literature, such as inorganic materials, modified natural products, or synthetic organic polymers. In Yim (loc. cit.), the binding of the antibodies occurs by covalent bonding between thiosemicarbazide and silica gel.

In view of the expanding role which carrier-bound antibodies play in biochemistry and medicine, there is a continued great demand for optimized carrier systems based on polymeric carriers, wherein the effectiveness of the antibodies bound to the carriers is reduced as little as possible, while maintaining the optimal stability, range of applicability and efficiency of the carrier system.

SUMMARY OF THE INVENTION

According, it is an object of the present invention to provide immobilized antibodies which retain their antigenic affinity, while providing an optimal stability, range of applicability and efficiency for the carrier system.

In particular, the present invention provides antibodies which are immobilized and covalently bound to a matrix polymer by means of a modification in the carbohydrate region of the antibodies, wherein the binding of the antibodies is effected by condensing at least one aldehyde group in an oxidized carbohydrate region and at least one epoxide function of an epoxy-group-containing matrix polymer, the condensation being conducted in the presence of a bifunctional reagent which has, on one end position of a spacer unit having at least three members, an amino group capable of condensing with the aldehyde group, and which has, on the other end position, a group which reacts covalently with the epoxide function.

DESCRIPTION OF THE PREFERRED EMBODIMENTS

The present invention relates, as noted above, to immobilized antibodies which are covalently bonded, via their modified carbohydrate region, to a matrix polymer, wherein the binding of the antibodies is effected by condensing at least one aldehyde group of an oxidized carbohydrate region and at least one epoxide function of a reactive epoxy-group-containing matrix polymer (MP) by the intermediary of a bifunctional reagent (BR) which bears, on one end position of a spacer unit having at least three members, an amino group capable of condensing with the aldehyde group, and which bears on the other end position a group which reacts covalently with the epoxide function.

The Matrix Polymer (MP):

The MP is desirably a crosslinked copolymer of (meth)acrylamide and glycidyl (meth)acrylate, preferably in bead form. Such MPs are described in Ger. Pat. No. 2,722,751, and U.S. Pat. Nos. 4,190,713 and 4,511,694, which U.S. patents are incorporated herein in the entirety. The beads generally have a diameter of 5–1000 microns, particularly 30–1000 microns, and have an inner hollow space, i.e., they are hollow beads. As a guideline for the content of glycidyl groups available for reaction in the MP, about 0.8–2.5 μmol per mg dry carrier material is available. Additional characterizing parameters for a common commercially available MP (Eupergit C ®, of Roehm GmbH), typical of MPs of the specified general type, may be obtained from the following Table:

| | |
|---|---|
| Mean particle size | 140–180 micron |
| Pore diameter | 40 nm |
| Exclusion limit (=$M_{LIM}$) | $2 \times 10^5$ Dalton |
| Binding-active surface | 180 m²/g (dry) |
| Epoxide content | 800–1000 mmol/g dry weight |
| Water uptake | 2.3 ml/g (dry) |
| Specific gravity, $d_4^{20}$ | 1.20 |
| Bulk density | 0.34 g/ml |
| Combining capacity (under ordinary conditions): | |
| - Human albumin | 48 mg/g (moist) |
| - Human IgG | 34 mg/g (moist) |
| Swelling by water | 40% (1 l dry yields 1.4 ml moist) |
| Solubility in water, buffers, and organic solvents | Insoluble |
| Pressure stability | 300 bar |

Under an electron microscope the macroporous structure of the beads can be observed, with channels and voids having a diameter of 1,000–25,000 Å, so that enzyme and substrate molecules with a size of 10–100 Å can reach the entire interior of the macroporous matrix.

Site-Specific Modification of the Antibodies:

In accordance with the present invention any antibody may be used which has carbohydrate groups and which is amenable to chemical modification and subsequent fixing. As an estimate, a content of about 3% carbohydrate in the antibodies is adequate. Most advantageously, however, monoclonal antibodies are used. Methods of producing monoclonal antibodies are well known. See Kirk-Othmer "Encyclopedia of Chemical Technology", 3rd Ed., V. 23 (1983), pub. John Wiley, pp. 647–643; Baron, D., and Hartlaub, U., 1987, "Humane moleculare Antikoerper", pub. Gustav Fischer Verlag, Stuttgart and New York.

The following procedure may be used. Prior to oxidation, the lymphocytes or monoclonal antibodies are first purified by, e.g., positive purification techniques such as affinity chromatography, or negative purification (cleaning) techniques to eliminate additional other cells, such as panning, complement lysis, and E-rosetting. Then the lymphocytes or monoclonal antibodies are preferably dialyzed, e.g. using a suitable compatible buffer, in a pH range near 5.5. The oxidation of the carbohydrate content to formyl groups may be carried out chemically in known fashion by periodate oxidation, or, less preferably, enzymatically by means of the enzymes galactose oxidase and catalase.

By operating at relatively low pH, such as about 5.0–6.0, preferably near 5.5, or about 5.0–5.5, the risk of internal crosslinking of the antibodies is reduced or eliminated. A preferred oxidation method consists of oxidation with sodium periodate, preferably 0.1 M, in a suitable inert buffer solution, advantageously in the pH 5.5 range, e.g. in 0.1 M acetate buffer. Preferably the reaction is carried out at relatively low temperature, e.g. 0° –5° C., and in darkness.

The oxidation, which ordinarily can be completed in approximately 1 hr, is terminated, e.g. by the addition of a small amount of ethylene glycol. The antibodies are advantageously processed on a gel chromatography column. (See "Ullmanns Encyklopaedie der techn. Chemie", 4th Ed., Vol. 5, pub. Verlag Chemie, p. 167; and "Gel filtration, theory and practice", in 1979 "Pharmacia fine chemicals", pub. Deutsche Pharmacia GmbH, Freiburg, FRG.) A suitable material for this is, e.g., a dextran gel (e.g., Sephadex G 25 ® of the firm Pharmacia), preferably equilibrated with a buffer solution in the pH 5 range. The antibodies can be concentrated by a technique such as ultrafiltration. Ordinarily the yield of antibodies is >90%.

Coupling of the Site-Specifically Modified Antibodies to Polymeric Carriers:

The recovered oxidized and purified antibodies are incubated in a suitable slightly acid medium, for example, in acetate buffer and in a pH range near 5.5, in amounts between 60 and 200 μg, with 100 mg of the hydrazide-substituted modified polymeric carrier ("HY-MP"), for a given period, e.g. 16 ±4 hr, at reduced temperature, e.g. 4° C. The proportion of immobilized antibodies is determined by the method of Bradford (*Analyt. Biochem.*, 72, 248 (1976)), from the difference between the original and the residual content of antibodies.

The antibodies bound to the hydrazine derivatives have an enhanced antigen combining capacity compared to that of antibodies bound to unmodified polymeric carrier ("P"). That enhanced combining capacity approaches the theoretical maximum of 2 mol antigen per mol antibodies, particularly when the concentration of antibodies is relatively low.

Modification of the Matrix Polymer (MP):

The MP is comprised of (meth)acrylamide and glycidyl (meth)acrylate units, and is preferably in the form of beads, being particularly the product Eupergit C ® of Roehm GmbH, of Darmstadt. The MP is advantageously treated in a suitable buffer solution in the alkaline pH range, e.g. in a phosphate buffer at pH 8.8, for a specific time, e.g. 16 ±3 hr, at room temperature, with the bifunctional reagent BR, which is preferably a bishydrazide of an aliphatic dicarboxylic acid, particularly adipic acid dihydrazide. Preferably the BR is used in the amount of 0.1–10 mol per gram (dry weight) of the polymeric carrier MP, particularly Eupergit C ®, particularly 1 μmol BR per gram dry weight. Advantageously, the modified matrix polymer HY-MP is washed with standard phosphate buffer (PBS). Preferably, equilibrium at pH 5.5 is established with buffer (e.g. 0.1 M acetate buffer), and the material is stored at low temperature, e.g. 4° C.

The Bifunctional Reagent (BR):

The BR is defined as being comprised of a unit having at least 3 members and having a spacing function; further, having an amino group at one end position which group is capable of condensing with the aldehyde group, and having at the other end position a group which reacts covalently with the epoxide function of the MP. Preferably the BR has a formula which can be represented as:

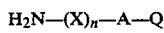

where A represents a spacer, preferably an alkyl or cycloalkyl group, having 3 to 12 chain members which are preferably —$CH_2$— units, wherewith one or more of the chain members may be oxygen;

where n is 0 or 1;

where X represents one of the following groups:

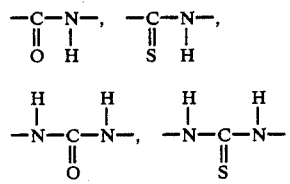

and where Q is —X—$NH_2$ or —$NH_2$.

Particularly preferred as the BR is the bishydrazide of a dicarboxylic acid, where A=$(CH_2)_{3-6}$, X=—CONH—, and Q=$XNH_2$, in particular adipic acid dihydrazide. If the BR is an alkylenediamine, where n=0, A=$(CH_2)_{3-6}$, Q=$NH_2$, the double bond of the Schiff base formed in the condensation is advantageously reduced, e.g. with sodium borohydride.

Determination of the Immunocapacity of the Inventively Fixed Antibodies:

The combining capacity of the inventively immobilized antibodies is determined by measuring the antigens, which are in particular enzymes such as anticarboxypeptidase (CPA), which combine with the antibodies. For this purpose, e.g., CPA is added to test tubes in equal amounts, in PBS, which test tubes each contain 100 mg of the modified matrix polymer HY-MP as well as differing amounts of immobilized monoclonal antibodies. The amount of CPA combined with the antibodies of the matrix polymer is determined as follows:

(Alpha) By determining the difference in protein content, using the Bradford test, and by the enzymatic activity difference between the starting and residual solutions;

(Beta) By determining the enzymatic activity of the CPA enzyme immobilized on the HY-MP carrier beads, e.g. with the aid of the ninhydrin method. The amount of enzyme bound on the carrier is eluted, after incubation, with sodium carbonate buffer at pH 10.5. After pH adjustment, the activity of the eluted enzyme, e.g. CPA, is determined.

Determination of enzyme activity is used in all cases where the antibodies present do not materially reduce the enzymatic activity. It turns out that the oxidatively modified antibodies which are fixed to the HY-MP carrier beads retain their full immunologic activity for combining with the enzyme (e.g. CPA).

The molar ratio of monoclonal antibodies to CPA varies in the range 2:1 to 1:1.

As noted above, the present invention generally encompasses conjugates of oligosaccharide-containing antibodies. Particularly noteworthy are monoclonal antibodies which are directed against a wide variety of antigens. The following exemplify the diversity of antigens:

Bacterial antigens: Tetanus toxoid; H. influenzae type b polysaccharide; Diphtheria toxin; Chlamydia trachomatis; M. leprae; Lipopolysaccharide endotoxin; Pneumococci; LPS of P. aeruginosa; Exotoxin of P. aeruginosa; Streptococci group A carbohydrate.

Viral antigens: X31 influenza virus nucleoprotein; Measles (rubeola) virus; HSV glycoprotein D; Measles virus nucleocapsid; Cytomegaly virus; Influenza A viruses; Rubella virus antigen; HTLV I; Varicella zoster; HBsAg.

Autoimmune antigens: Double strand DNA; Insulin cells (diabetes mellitus); Myasthenia gravis antiidiotypes; Thyrotropin (TSH) receptor; Rheuma factor; Acetylcholine receptor; Thyroid extract; Semen.

Tumor antigens: Mammary carcinoma; Prostate carcinoma; Lung carcinoma; Gastric carcinoma; Melanoma; GD2 (human melanoma); Glioma; Rectal carcinoma; Leukemia; Cervical carcinoma.

Tissue and blood antigens: Rhesus D; Blood group antigen A; HL-A antigens A, B, C, or DR; Intermediary filaments.

Other antigens: Malaria; Forssman antigen; Sheep erythrocytes; Nitrophenol; Dinitrophenol; Trinitrophenol; Keyhole limpet hemocyanin (KLH); Rheuma factor; Insulin.

The fixing of the present invention offers a number of advantages over conventional fixing techniques, particularly when dicarboxylic acid hydrazides are used, in particular adipic acid hydrazide. For example, if condensation is effected at a pH near 5.5, one prevents condensation of the amino groups of the antibodies with the aldehyde functions of the same antibodies.

The chemical binding via the hydrazide is stabile and inert, as desired. Non-specific binding of the antibodies is minimized. Any blocking survives the fixing of the antibodies.

The present invention will now be further illustrated by reference to the following nonlimitative examples.

EXAMPLE 1

Coupling of the aldehyde-group-containing monoclonal antibodies to the modified matrix polymer HY-MP as carrier.

Modified and oxidized monoclonal antibodies obtained from Example 2 (infra) were incubated in amounts ranging between 60 and 200 μg in 1 ml of a pH 5.5 acetate buffer with 400 microliter (100 mg) of the modified matrix polymer MP from Example 3, for 16 hr ar 4° C. The amount of immobilized antibodies was determined by the Bradford method from the difference between the original and surviving amounts of antibodies.

The fixed antibodies of the present invention had, in comparison to conjugates bound directly via the oxirane function, a higher antigen combining capacity (e.g. where CPA is the antigen). They approached the theoretical maximum value of two antigens per mol antibodies, particularly if the antibody concentration was small. See Table 2.

TABLE 2:

| | Binding of purified, oxidized monoclonal antibodies to matrix polymer HY-MP. | | | |
|---|---|---|---|---|
| Antibodies | Activated antibodies (mg) used per gram dry carrier MP | Antibodies bound (mg) per gram dry carrier MP | CPA antigen (mg) per gram carrier MP | Molar ratio of antigen to antibodies (mol/mol) |
| CPA 1 | 0.7 | 0.7 | 0.32 | 2.0 |
| CPA 6 | 0.5 | 0.5 | 0.30 | 2.5 |
| CPA 6 | 17.5 | 7.5 | 4.5 | 2.5 |
| CPA 7 | 1.0 | 0.7 | 0.34 | 2.1 |
| CPA 8 | 0.8 | 0.8 | 0.32 | 1.65 |
| CPA 8 | 25.0 | 13.0 | 4.40 | 2.5 |
| CPA 2 | 3.5 | 1.0 | 0.36 | 1.5 |
| CPA 3 | 2.2 | 1.0 | 0.40 | 1.7 |
| CPA 5 | 3.0 | 2.0 | 0.40 | 1.0 |

EXAMPLE 2

Preparation of the aldehyde-group-containing monoclonal anti-CPA antibodies.

A series of affinity-chromatographically purified monoclonal anti-CPA antibodies was dialyzed prior to the periodate oxidation, against 0.1 M acetate buffer (pH 5.5). Each monoclonal antibody was treated with 0.1 M sodium periodate dissolved in 10 ml 0.1 M acetate buffer (pH 5.5). At this low pH, internal crosslinking of the antibody molecules was suppressed. The reaction was carried out for 1 hr at 0° C., in darkness.

The oxidation was terminated by addition of 3 drops ethylene glycol, and the reaction mixture was then fed to a column of Sephadex G 25 ® which had been pre-equilibrated with 0.1 M acetate buffer (pH 5). The oxidized antibodies were concentrated in a 10 ml Amicon ultrafiltration cell equipped with a PH 50 membrane, and the protein content was determined by the Bradford method. The recovery of the antibodies was typically >90%.

EXAMPLE 3

Modification of the matrix polymer MP.

2 g of the crosslinked methacrylamide/glycidyl methacrylate copolymer (Eupergit C ®, product of Roehm GmbH, of Darmstadt) was treated with 0.1 M commercial adipic acid dihydrazide in 20 ml of a 0.2 M phosphate buffer (pH 8.8) for 16 hr at room temperature. The modified polymeric carrier was thoroughly washed with PBS (standard phosphate buffer), was equilibrated with 0.1 M acetate buffer (pH 5.5), and was stored at 4° C.

Having now fully described the present invention, it will be apparent to one of ordinary skill in the art that many changes and modifications can be made thereto without departing from the spirit or scope of the invention as set forth herein.

What is claimed as new and desired to be secured by letters patent of the U.S. is:

1. Antibodies which are immobilized and covalently bound to a matrix polymer through the carbohydrate region wherein; the binding of the antibodies is effected by condensing at least one aldehyde group, formed by periodate oxidation, with at least one epoxide function of an epoxy-group containing matrix polymer; said condensation being conducted in the presence of a bifunctional reagent of formula

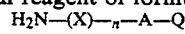

wherein;

A represents a spacer which is an alkyl or cycloalkyl group having 3 to 12 carbon atoms, or one or more of which carbon atoms are replaced by oxygen atoms;

where n is 0 or 1;

where X represents on one of the following groups:

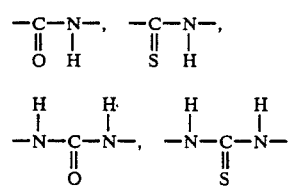

and where Q is —X—NH₂ or —NH₂.

2. The immobilized antibodies according to claim 1, wherein the periodate oxidation is carried out at pH 5-5.5.

3. The immobilized antibodies according to claim 1, wherein ethylene glycol is used to terminate the oxidation.

4. The immobilized antibodies according to claim 1, wherein a compound having the following formula is used as the bifunctional reagent:

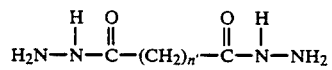

where n' represents 3 to 6.

5. The immobilized antibodies according to claim 1, wherein a copolymer comprising (meth)acrylamide and glycidyl (meth)acrylate units is used as the epoxy-group-containing matrix polymer.

6. The immobilized antibodies according to claim 1, wherein the reaction product of a bifunctional reagent according to claim 5 with a matrix polymer according to claim 7, at pH 8.8-9, is prepared.

7. The immobilized antibodies according to claim 1, wherein the reaction product of a bifunctional reagent with the matrix polymer is condensed with the oxidized carbohydrate region of the antibodies.

8. The immobilized antibodies according to claim 7, wherein the reaction is carried out in the pH range 5-5.5.

9. A method of preparing immobilized antibodies by covalently binding the antibodies to a matrix polymer through the carbohydrate region of said antibodies wherein; the binding of the antibodies is effected by condensing at least one aldehyde group, formed by periodate oxidation, with at least one epoxide function of an epoxy-group-containing matrix polymer, said condensation being conducted in the presence of a bifunctional reagent of formula $$H_2N-(X)-_n-A-Q$$

wherein
  A represents a spacer which is an alkyl or cycloalkyl group having 3 to 12 carbon atoms, or one or more of which carbon atoms are replaced by oxygen atoms;
  where n is 0 or 1;
  where X represents on one of the following groups:

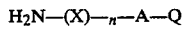

-continued

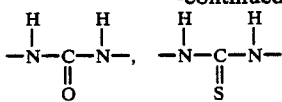

and
where Q is —X—NH$_2$ or —NH$_2$.

10. The method of preparing immobilized antibodies according to claim 9, wherein the periodate oxidation is carried out at pH 5-5.5.

11. The method of preparing immobilized antibodies according to claim 9, wherein ethylene glycol is used to terminate the oxidation.
where Q is —X—NH$_2$ or —NH$_2$.

12. The method of preparing immobilized antibodies according to claim 9, wherein a compound having the following formula is used as the bifunctional reagent:

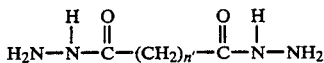

where
  n' represents 3 to 6.

13. The method of preparing immobilized antibodies according to claim 9, wherein a copolymer comprising (meth)acrylamide and glycidyl (meth)acrylate units is used as the epoxy-group-containing matrix polymer.

14. The method of preparing immobilized antibodies according to claim 9, wherein the reaction product of a bifunctional reagent according to claim 15 with a matrix polymer according to claim 17, at pH 8.8-9, is prepared.

15. The method of preparing immobilized antibodies according to claim 9, wherein the reaction product of a bifunctional reagent with the matrix polymer is condensed with the oxidized carbohydrate region of the antibodies.

16. The method of preparing immobilized antibodies according to claim 15, wherein the reaction is carried out in the pH range 5-5.5.

* * * * *